United States Patent [19]
Atkinson

[11] Patent Number: 5,542,918
[45] Date of Patent: Aug. 6, 1996

[54] VACUUM DRIVEN FLUID PUMP FOR AN ASPIRATION/IRRIGATION INSTRUMENT

[75] Inventor: Robert W. Atkinson, Dover, Ohio

[73] Assignee: Zimmer, Inc., Warsaw, Ind.

[21] Appl. No.: 369,232

[22] Filed: Jan. 6, 1995

[51] Int. Cl.⁶ .............................. A61M 3/00; F04B 17/00
[52] U.S. Cl. .............................. 604/27; 604/35; 417/401
[58] Field of Search .................................. 417/390, 401, 417/395, 398, 399; 604/27, 30, 33, 35, 131, 135, 902; 60/370

[56] References Cited

U.S. PATENT DOCUMENTS

| | | | |
|---|---|---|---|
| 1,390,617 | 9/1921 | Jay | 417/401 |
| 1,743,968 | 1/1930 | Hatfield | 417/401 |
| 2,510,649 | 6/1950 | Neff | 417/401 |
| 3,134,304 | 5/1964 | Hager | 91/341 |
| 3,482,766 | 12/1969 | Rehfeld | 417/401 |
| 3,700,359 | 10/1972 | Vanderjagt | 417/404 |
| 4,193,264 | 3/1980 | Takahashi et al. | 417/401 |
| 4,776,840 | 10/1988 | Freital et al. | 604/33 |
| 5,195,958 | 3/1993 | Phillips | 604/27 |

FOREIGN PATENT DOCUMENTS 2063674  6/1981  United Kingdom ...................... 604/30

Primary Examiner—John J. Vrablik
Assistant Examiner—Roland G. McAndrews, Jr.
Attorney, Agent, or Firm—Todd A. Dawson

[57] ABSTRACT

A fluid pump 20 used in a lavage instrument 10 that is driven by vacuum pressure is disclosed. Fluid pump 20 includes a fluid housing 30 connected to an external fluid source and a pneumatic cylinder 50 connected to an external vacuum source. A diaphragm 40 is shiftably disposed within fluid housing 30 to define an inner fluid chamber 31. Pneumatic cylinder 50 includes a cylinder casing 60 and a reciprocating piston 70, which defines a vacuum chamber 61. Piston 70 includes a poppet valve 80 and is connected to diaphragm 40 by two push rods 68. Negative pressure within vacuum chamber 61 draws piston 70 forward and compresses a return spring 67. As piston 70 is drawn forward, piston 70 pushes diaphragm 40 forward to expel fluid from fluid chamber 31 through an outlet port 36. Piston 70 is drawn forward until poppet valve 80 is unseated by its engagement with a post 66 which extends longitudinally from casing end wall 44. Unseating poppet valve 80 equalizes the pressure within vacuum chamber 61 and allows return spring 67 to push piston 70 and diaphragm 40 rearward. Fluid is drawn into fluid chamber 31 through an inlet port 34 by the rearward movement of diaphragm 40. During the rearward stroke of piston 70, poppet valve 80 is reseated and vacuum pressure is reestablished within the vacuum chamber.

5 Claims, 4 Drawing Sheets

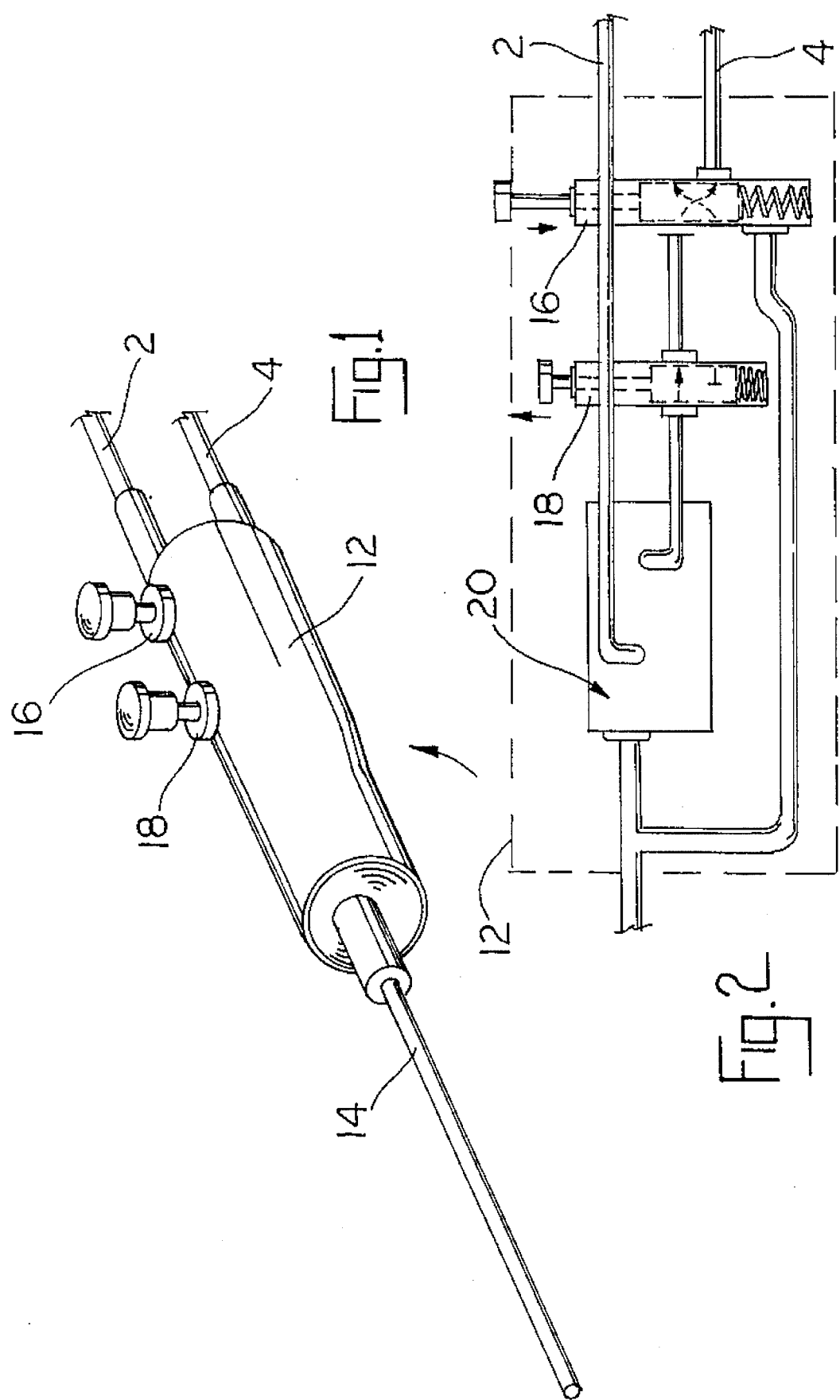

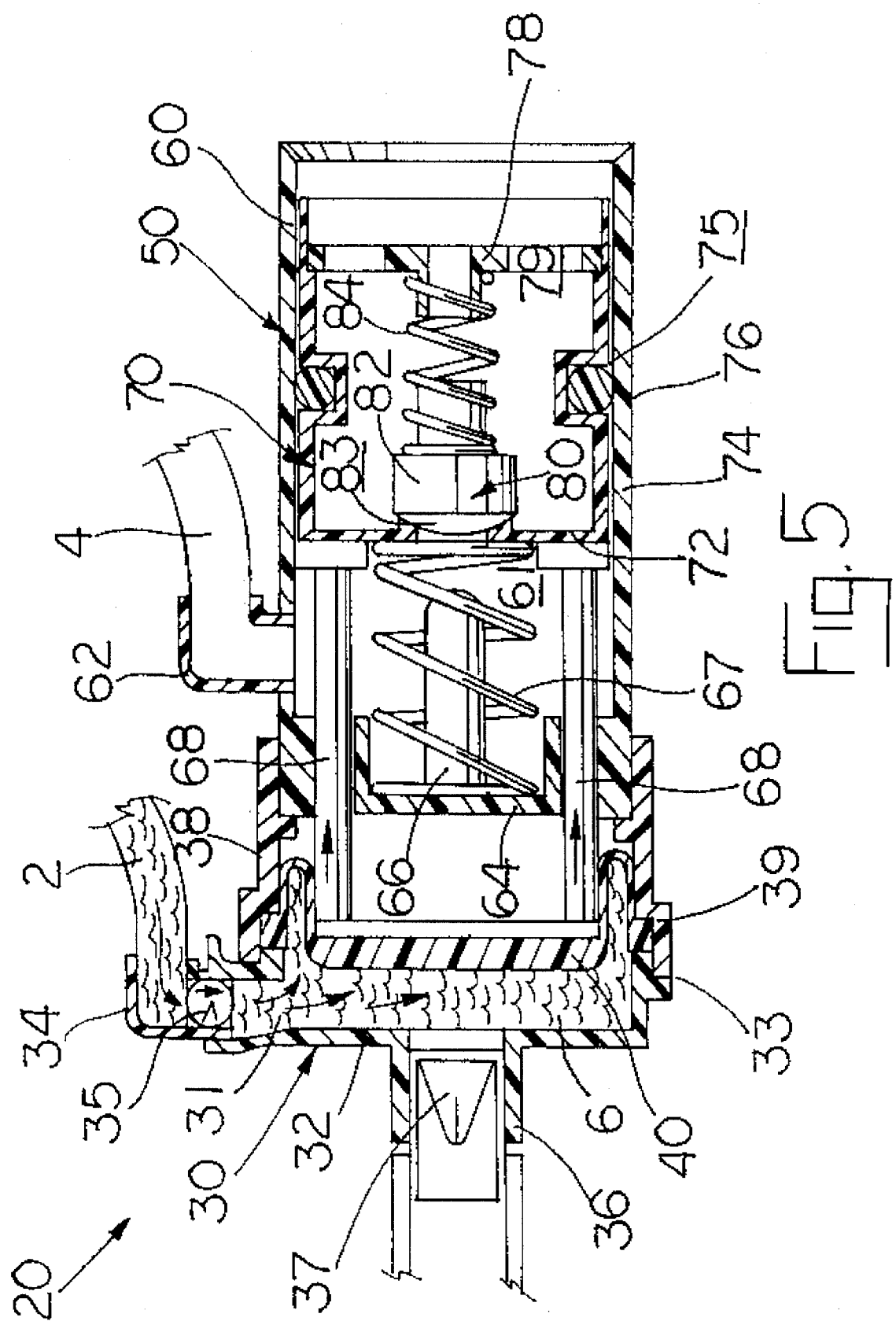

VACUUM DRIVEN FLUID PUMP FOR AN ASPIRATION/IRRIGATION INSTRUMENT

This invention elates to a fluid pump and has specific relevance to a vacuum driven fluid pump used in a lavage instrument.

BACKGROUND OF THE INVENTION

In many medical and surgical procedures, irrigating wounds, and surgical areas with fluids and/or removing various irrigating fluids from the surgical area is often necessary. Lavage instruments are well known in the medical arts. Lavage instruments have been developed, which are connected to an external vacuum source to additionally provide an aspiration function. Typically, lavage instruments have been connected to external fluid pumps, which supply irrigation fluids to the lavage instrument from an external fluid source, such as a hanging fluid bag. Heretofore, lavage instruments that include internal fluid pumps have been electrically powered, which increases the size, weight and cost of the lavage instrument. It is desirable to develop a lavage instrument, which includes an internal fluid pump that is lightweight, inexpensive, disposable and driven by an alternative power source.

SUMMARY OF THE INVENTION

The fluid pump of this invention is used in a lavage instrument which is driven by vacuum pressure supplied by an external vacuum source. The vacuum driven fluid pump is well suited for lavage instruments that are already connected to an external vacuum source to provide aspiration functions.

The fluid pump of this invention includes a fluid housing connected to an external fluid source and a pneumatic cylinder connected to an external vacuum source. A diaphragm is shiftably disposed within the fluid housing to define an inner fluid chamber The pneumatic cylinder includes a cylinder casing and a reciprocating piston, which defines a vacuum chamber. The piston includes a popper valve and is connected to the diaphragm by two push rods. Negative pressure within the vacuum chamber draws the piston forward and compresses a return spring. As the piston is drawn forward, the piston pushes the diaphragm to expel fluid from the fluid chamber through an outlet port. The piston is drawn forward until the poppet valve is unseated by its engagement with a post, which extends longitudinally from the cylinder casing's end wall. Unseating the poppet valve equalizes the pressure within the vacuum chamber and allows the return spring to push the piston and the diaphragm rearward. Fluid is drawn into the fluid chamber through an inlet port by rearward movement of the diaphragm. During the rearward stroke of the piston, the poppet valve is reseated and vacuum pressure is reestablished within the vacuum chamber. The resulting reciprocal movement of the piston and connected diaphragm produces a constant oscillating fluid flow.

Accordingly, an advantage of this invention is to eliminate the need to connect a lavage instrument to an external fluid pump.

Another advantage of this invention is to provide an internal fluid pump used in a handheld lavage instrument, which is driven by vacuum pressure supplied from an external vacuum source.

Another advantage is to reduce the size and weight of a handheld lavage instrument, which includes an internal fluid pump, by using a fluid pump that is powered by vacuum pressure from an external vacuum source.

Other advantages will become apparent upon a reading of the following description.

BRIEF DESCRIPTION OF THE DRAWINGS

A preferred embodiment of the invention has been depicted for illustrative purposes only wherein:

FIG. 1 is a perspective view of a lavage instrument, which uses the fluid pump of this invention.

FIG. 2 is the internal layout of the lavage instrument of FIG. 1;

FIG. 5 is a sectional view of the fluid pump of this invention showing the rearward stroke of the piston and diaphragm.

DESCRIPTION OF THE PREFERRED EMBODIMENT

Figure 3:
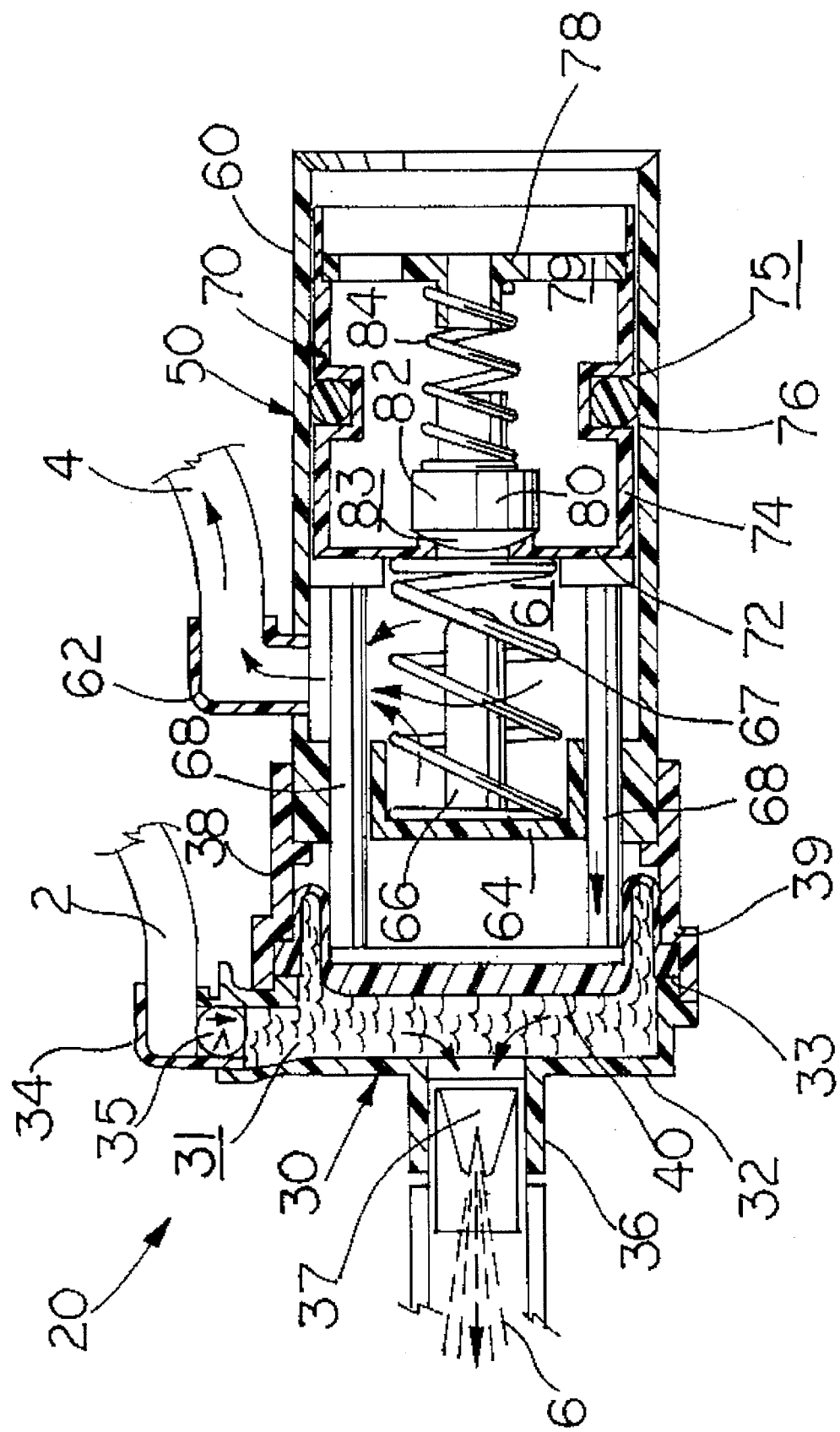
FIG. 3 is a sectional view of the fluid pump of this invention showing the forward stroke of the piston and diaphragm.

The preferred embodiment herein described is not intended to be exhaustive or to limit the invention to the precise form disclosed. It is chosen and described to explain the principles of the invention and its application and practical use to enable others skilled in the art to utilize its teachings.

FIGS. 1 and 2 show the lavage/aspiration instrument 10 used to selectively irrigate and aspirate fluid from a wound or surgical area, which includes the fluid pump 20 of this invention. While the fluid pump of this invention is used in a lavage/aspiration instrument, fluid pump 20 can be easily modified for a variety of lavage instruments and applications.

As shown in FIGS. 1 and 2, instrument 10 includes a body 12 which encloses fluid pump 20, elongated hollow probe 14, and two trumpet valves 16, 18. Instrument 10 is connected to an external fluid source, such as a hanging fluid bag (not shown) by a fluid line 2 and to an external vacuum source (also not shown) by a vacuum line 4. As shown in FIG. 2, fluid line 2 is connected directly to fluid pump 20 and vacuum line 4 is connected to trumpet valve 16. Trumpet valve 14 selectively communicates vacuum pressure between probe 14 (FIG. 1) and trumpet valve 18. When its piston is depressed, valve 16 communicates vacuum pressure to probe 14 (FIG. 1) to aspirate fluid from the wound or surgical site. When its piston is released, valve 16 communicates vacuum pressure to trumpet valve 18. Trumpet valve 18 is connected to fluid pump 20. When its piston is depressed, valve 18 is open and communicates vacuum pressure to fluid pump 20 to operate the fluid pump. When its piston is released, valve 18 is closed and suspends the operation of the fluid pump.

Figure 4:
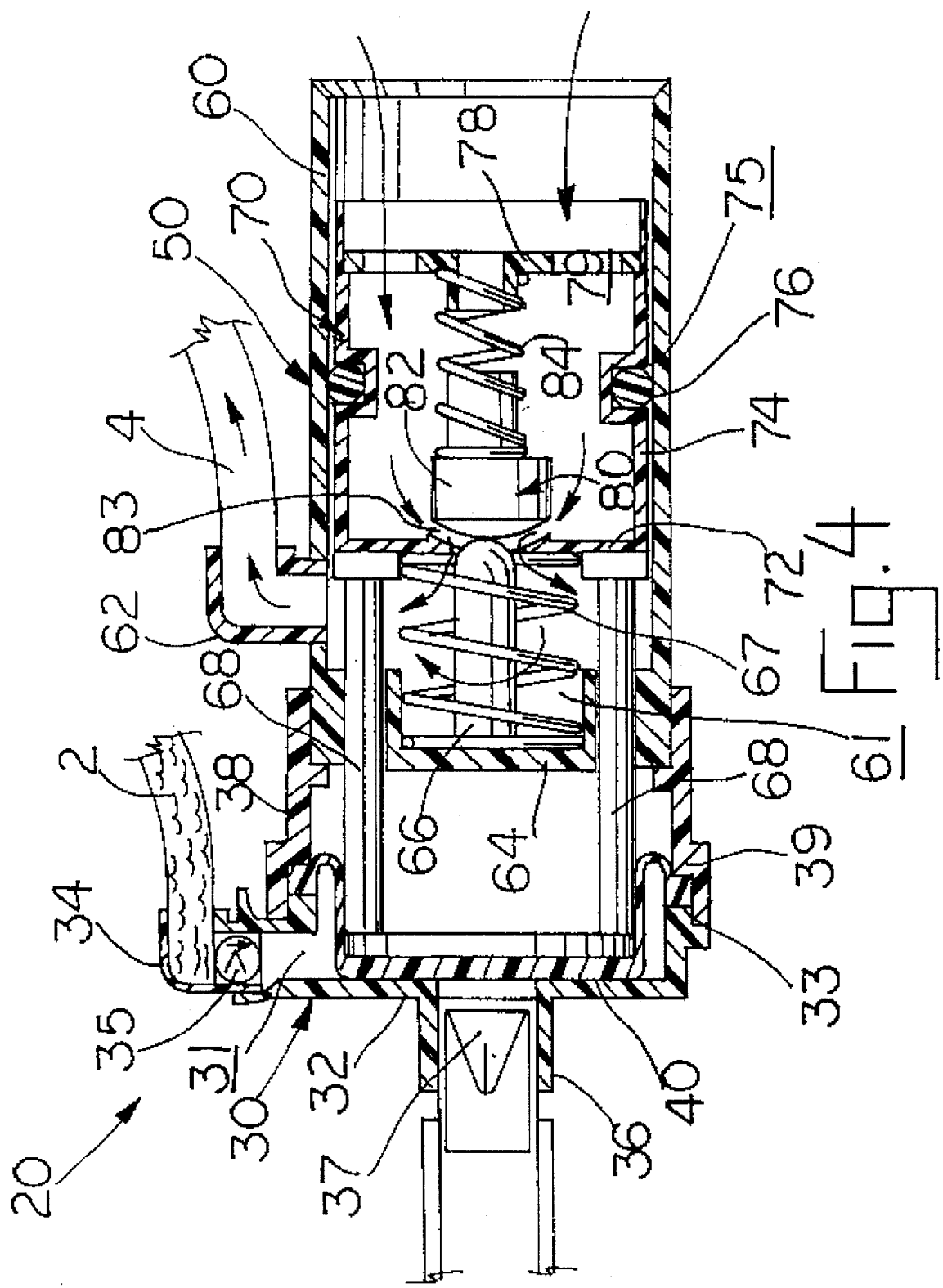
FIG. 4 is a sectional view of the fluid pump of this invention showing the piston and diaphragm at the top of their forward stroke.

Referring now to FIGS. 3-5, fluid pump 20 includes a fluid housing 30 and a pneumatic vacuum cylinder 50. Fluid housing 30 includes an anterior section 32 and collar section 38. A diaphragm 40 is restrictively seated between anterior section 32 and collar section 38 to define an inner fluid chamber 31. Preferably, diaphragm 40 is constructed of a butyl rubber or other suitable material. As shown, the peripheral edge of diaphragm 40 is held between a shoulder 33 formed in anterior section 32 and a shoulder 39 formed in collar section 38. Anterior Section 32 includes an inlet port 34 connected to a fluid line 2, and an outlet port 36 connected to a probe 14 (FIG. 1). Inlet port 34 includes a one-way valve 35, which allows fluid to enter fluid chamber 31. Outlet port 36 includes a second one-way valve 37, which allows fluid to exit fluid chamber 31.

Pneumatic cylinder 50 includes a cylinder casing 60 and a reciprocating piston 70, which defines a vacuum chamber 61. Cylinder casing 60 includes a port 62 connected to a vacuum line 4, which communicates freely with vacuum chamber 61. Cylinder casing 60 also includes a longitudinal post 66, which extends toward piston 70 from its end wall 64. A helical spring 67 is seated around post 66 and against cylinder end wall 64 and piston 70. As shown in FIGS. 3–5, piston 70 is connected to diaphragm 40 by two push rods 68, which extend transversely through bores in cylinder end wall 64. Piston 70 includes an anterior wall or head 72 and a cylindrical skirt 74. Skirt 74 has an annular recess 75. An O-ring 76 is disposed within recess 75 for hermetically sealing vacuum chamber 61. A partition 78 is connected to the posterior end of piston 70 and has a plurality of vents 79 for open communication with the outside atmosphere. Piston 50 also includes a poppet valve 80. Popper valve 80 includes a poppet 82, which is seated in a valve opening 83 formed in piston head 72. Poppet 82 is held against valve opening 83 by a helical spring 84 compressed between poppet 82 and partition 78.

FIGS. 3–4 illustrate the operation of fluid pump 20. As shown in FIG. 3, vacuum pressure within vacuum chamber 61 draws piston 70 forward and compresses spring 67. The forward stroke of piston 70 pushes diaphragm 40 forward to expel fluid 6 from fluid chamber 31 through one-way valve 37 of outlet port 36. One-way valve 35 prevents fluid from being expelled through inlet port 34. As shown in FIG. 4, piston 70 is drawn forward until popper 82 is unseated by its engagement with post 66. When popper 82 is unseated, pressure within vacuum chamber 61 is equalized by open communication with the outside atmosphere through valve opening 83 and partition vents 79. As shown in FIG. 5, once pressure within vacuum chamber 61 is equalized with the outside atmosphere, the tension of spring 67 propels piston 70 and diaphragm 40 backwards. The rearward stroke of piston 70 and diaphragm 40 draws fluid into fluid chamber 31 through inlet pod 34 and valve 35. As piston 70 moves away from post 66, spring 67 reseats poppet 82 against valve opening 83 to reestablish vacuum pressure within vacuum chamber 61. The resulting reciprocal movement of piston 70 and diaphragm 40 produces a constant pulsatile fluid flow.

It is understood that the above description does not limit the invention to the details given, but may be modified within the scope of the following claims.

I claim:

1. A hand held lavage instrument for use with an irrigation fluid source and a vacuum source for directing an irrigating fluid from said fluid source and an aspirating suction from said vacuum source to a surgical site, said instrument comprising:

a body, a probe extending from said body, a fluid pump carded by said body and connected to said fluid source and said vacuum source, and valve means carded by said housing and connected between said fluid pump and said vacuum source for selectively communicating negative pressure from said vacuum source to one of said fluid pump and said probe, wherein with said vacuum source connected to said fluid pump, said fluid pump operates to pump the irrigating fluid from said fluid source through said probe to said surgical site, and wherein with said vacuum source connected to said probe said vacuum source aspirates material from said site through said probe to aspirate said surgical site, said fluid pump includes a housing having a fluid chamber for receiving fluid from said fluid source, a diaphragm part disposed within said fluid chamber for reciprocal movement therein, and a pneumatic cylinder connected to said vacuum source for reciprocating said diaphragm part within said fluid chamber to draw fluid into said fluid chamber from said fluid source and to expel fluid from said fluid chamber.

2. The instrument of claim 1 wherein the valve means includes a trumpet valve shiftable between a first and second position, wherein with said trumpet valve in said first position, said vacuum source is connected to said fluid pump, and with said trumpet valve in its second position, the vacuum source is in flow communication with said probe.

3. The instrument of claim 1 wherein said pneumatic cylinder includes a cylinder casing having a vacuum chamber, and a piston part shiftably disposed within said vacuum chamber for reciprocal movement therein, said cylinder casing is connected to said vacuum source to create a negative pressure within said vacuum chamber for reciprocating said piston part within said vacuum chamber, said piston part is connected to said diaphragm part.

4. The instrument of claim 3 wherein said pneumatic cylinder includes a spring positioned within said vacuum chamber and compressively engaged against said piston part, and a valve connected to outside atmosphere and having a closed position and an open position, said piston part is moved in one direction to compress said spring by negative pressure within said vacuum chamber when said valve is closed and moved in the opposite direction by said spring when said valve is open.

5. The instrument of claim 3 wherein said piston part is connected to said diaphragm part by a rod part.

* * * * *